United States Patent [19]

Nicholas et al.

[11] Patent Number: 5,462,589
[45] Date of Patent: Oct. 31, 1995

[54] SYNERGISTIC WOOD PRESERVATIVE COMPOSITIONS

[75] Inventors: Darrel D. Nicholas; Tor P. Schultz, both of Starkville, Miss.

[73] Assignee: Mississippi Forest Products Laboratory, Starkville, Mich.

[21] Appl. No.: 200,173

[22] Filed: Feb. 22, 1994

[51] Int. Cl.$^6$ .............................. C08K 3/18; C08K 5/02; C08K 5/16; C09D 5/00
[52] U.S. Cl. .................... 106/18.33; 106/15.05; 106/18.35; 252/380; 252/384; 252/405; 252/406; 424/405; 424/630; 424/632; 424/633; 424/634; 424/635; 424/637; 424/638; 514/335; 514/500; 514/751
[58] Field of Search ............... 106/18.33, 18.35, 106/15.05; 514/499, 500, 335, 751; 252/405, 380, 384, 406; 424/405, 630, 632, 633, 634, 635, 637, 638

[56] References Cited

U.S. PATENT DOCUMENTS

| | | | |
|---|---|---|---|
| 1,803,870 | 5/1931 | Sanders | 424/638 |
| 1,866,069 | 7/1932 | Wilcoxon | 424/633 |
| 2,557,062 | 6/1951 | Pickren | 424/638 |
| 3,417,185 | 12/1968 | Herschler | 514/492 |
| 3,502,777 | 3/1970 | Burkhardt et al. | 514/494 |
| 3,993,752 | 11/1976 | Stutz | 424/610 |
| 4,276,308 | 6/1981 | Ito et al. | 514/521 |
| 4,379,810 | 4/1983 | Amundsen et al. | 428/541 |
| 4,388,215 | 6/1983 | Ishida et al. | 252/402 |
| 4,508,568 | 4/1985 | Fox | 106/2 |
| 4,783,221 | 11/1988 | Grove | 106/18.22 |
| 4,929,454 | 5/1990 | Findlay et al. | 424/638 |
| 5,009,700 | 4/1991 | Rothgery | 504/191 |
| 5,319,000 | 6/1994 | O'Connor et al. | 523/122 |

*Primary Examiner*—Anthony Green
*Attorney, Agent, or Firm*—Fish & Richardson

[57] ABSTRACT

The invention is directed to synergistic biocidal compositions that combine a copper salt and an organic biocide selected from the group of tribromophenol, its salts and chelates, and sodium-omadine, its salts and chelates. Wood treated with the preservative compositions have improved fungi resistance.

7 Claims, No Drawings

SYNERGISTIC WOOD PRESERVATIVE COMPOSITIONS

BACKGROUND OF THE INVENTION

The present invention relates generally to wood preservative compositions, and more particularly to synergistic biocidal compositions that combine low cost copper salts and organic biocides to preserve wood.

Wood is an important building and construction material and its importance and use continues to increase. Examples of its uses include general construction, residential housing, utility poles, crossing arms, fence posts, railroad ties and pilings, etc. For its various uses, wood must be protected from attack by insects, fungi and other organisms. Insects, such as termites, beetles and carpenter ants, cause extensive and costly damage to wood structures. Wood-attacking fungi, such as brown-rot and white-rot, will structurally weaken wood by damaging the cellulose and lignin. If left unprotected or unpreserved, wood will decay and deteriorate within a period of a few months to a few years, depending upon climate and soil conditions. Wood objects such as utility poles and timbers will deteriorate rapidly below ground level and will require frequent replacement if not properly and adequately preserved by chemical preservative treatment.

Toxicity to various wood-attacking organisms is an essential requirement of wood preservatives. The preservative treatments for wood must effectively repel attacking organisms for an extended period, i.e., provide long lasting protection. In addition, wood preservatives should have favorable wood penetrating properties, should not corrode metals and should be safe to handle by those treating the wood and using the furnished wood product.

Through the years, a number of different compounds have been used for preserving wood. Among these compounds include creosote, heavy metal salts, heavy oils and tars, pitch and various organic chemicals. Each of these compounds has its advantages and drawbacks.

For instance, creosote, as well as other heavy oils, tars and pitch treatments, has a strong odor and leaves the surface greasy and oily to the touch making the treated wood more difficult to handle. Halogenated phenols are also widely used as commercial wood preservatives because they have good fungicidal and insecticidal properties. The halogenated phenols are dissolved in hydrocarbon solvents, such as medium aromatic oils, volatile petroleum solvents (propane), light solvents (mineral spirits), or in a chlorinated hydrocarbon solvent-inhibited grade of methylene chloride.

Pentachlorophenol is a commonly used phenol preservative due to its effectiveness, relative ease of application and durability. However, recent environmental concerns are expected to limit the use of pentachlorophenol in the future. Copper and other heavy metals are good biocides. However, copper is not effective as a wood preservative since it does not control *Postia sp.* and other fungi which are copper tolerant.

Wood preservatives can be applied to wood as solutions, emulsions, pastes or dispersions in liquid hydrocarbons and/or aqueous systems. Water-borne preservatives are usually less expensive. In many applications, the use of water-borne preservatives are preferred, because of the odors, flammability and often toxic nature of liquid hydrocarbon solvents.

The protection afforded by the application of any wood preservative is dependent upon the depth and uniformity of the penetration into the wood or timber. The treatment of wood material usually comprises soaking or impregnating the wood with the fluid-borne treating chemicals. Another technique that is practiced in a number of variants is the full-cell process, where the pores of the wood material are partially evacuated before impregnation in order to increase the fluid retained therein, or the empty-cell process which is similar to the full-cell process except that the preliminary step of evacuation is omitted.

The most common commercial procedures for impregnating wood involve contacting the wood with the preservative under a relatively high pressure, for example, 50–200 psi (pounds per square inch) for a period of time, such as from one-half hour to twenty four hours. The processing may also require relatively high temperatures in the range from about 75° C. to about 105° to 110° C.

Upon contact and penetration into wood materials and during the drying process, the preservative in the wood preferably becomes fixed and essentially non-leachable. In various formulations, water in widely varying percentages is used as the main solvent for the treating solution.

In the course of treating wood with different biocides, certain insects and fungi are found not to be repelled by particular chemical treatments. In order to protect against a broader range of such insects and fungi, combinations of preservatives are sometimes used. Some combinations of preservatives have been found to have a greater effective than the sum of their individual components, and are considered synergistic.

An object of the present invention is to provide copper salt and organic preservative compositions that have synergistic effects in treating wood.

Another object of the present invention is to provide combinations of preservatives that are highly effective and less costly to use.

Additional objects and advantages of the invention will be set forth in the description which follows, and in part will be obvious from the description, or may be learned by practice of the invention.

SUMMARY OF THE INVENTION

The present invention is directed to a synergistic biocidal composition comprising a copper salt with an organic biocide selected from the group consisting of tribromophenol (TBP), its salts and chelates, and sodium omadine, its salts and chelates. Wood treated with the preservative compositions of this invention are characterized by improved fungi resistance. It is found that the copper salts, such as copper sulfate, copper acetate or copper carbonate, in these treating systems provide additional fixation and preservative properties.

According to the present invention, it has been found that the addition of TBP (2,4,6-tribromophenol) to a copper salt preservative will control the copper tolerant fungi and will act synergistically to preserve wood. The combination of sodium omadine (sodium pyrithione, $C_6H_4NOSNa$ or 2-pyridenthiol-1-oxide, sodium salt) and a copper salt preservative also produces similar synergistic results.

The present combinations of preservatives have been found to have a greater effectiveness than the sum of their individual components at a given concentration. The present invention will also protect against a broader range of insects and fungi. In addition, the present formulations eliminate the need for arsenic and chromium in the preservative formu-

DETAILED DESCRIPTION OF THE INVENTION

The present invention will be described in terms of certain specific embodiments and examples.

As used herein, the term "synergism" is intended to include both an increased spectrum of activity (i.e., greater activity against a larger number of microorganisms), and/or increased activity (i.e., greater activity against specific organisms than that predicted by use of either agent alone). Both of these factors play an important role in the economy and commercial acceptance of a biocide. Increased activity of the combination permits the use of smaller amounts of biocides to achieve satisfactory control with resulting economies. Increasing the spectrum of activity permits wider use of the biocide in environments containing many and diverse microorganisms which must be controlled.

The compositions used in the method of the present invention may also contain other additives depending on the intended use for the composition. When the compositions of the present invention are used in preserving wood, other additives may be included which impart desirable properties to the treated wood. For example, the compositions may contain anti-foam agents, surfactants, antioxidants, flame retardant compositions, coloring agents, insecticides, deodorants, mobicides, wood stabilizing agents, etc. The amount of such optional additives included in the composition of the present invention may vary over a wide range, although amounts of about 0.1 to 10.0 percent of these compositions are generally satisfactory.

Although copper salt and sodium omadine, individually, are both water soluble, combining these two compounds results in a reaction that forms a water-insoluble complex that precipitates in water. A suitable organic solvent can be used to dissolve the complex and form the present preservative composition for treating wood. Alternatively, the complex can be emulsified in water by using a small amount of organic solvent and a suitable surfactant. First, the complex is dissolved in the organic solvent. Then the surfactant is added and an emulsion is formed in water by thoroughly stirring the mixture. Various known combinations of surfactants and solvents can be used to produce stable emulsions for treating wood. The preparation and treatment using a copper-sodium omadine emulsion is the least expensive method.

An application method called a "dual water-borne" treatment can be used. A water-borne system has the advantage of being low cost, environmentally less hazardous and non-flammable, as compared with an organic solvent-borne system. Example 1 below gives the formulations for a dual water-borne treatment based on parts by total weight:

EXAMPLE 1

|  | Broad Range | Preferred Range |
|---|---|---|
| Formula A |  |  |
| Copper | 0.25 to 10.0 | 0.5 to 3.0 |
| Water | 90 to 99 | 97 to 99 |
| Formula B |  |  |
| Sodium Omadine | 0.1 to 2.0 | 0.1 to 1 |

-continued

|  | Broad Range | Preferred Range |
|---|---|---|
| Water | 98 to 99 | 99 |
| Ratio of A to B (Copper to Sodium Omadine) | 20:1 to 1:2 | 10:1 to 2:1 |

The dual water-borne treatment is carried out by the sequential application of an aqueous sodium omadine solution (Formula B) followed by an aqueous copper salt solution (Formula A), or vice versa. In Formula A, the copper salt is dissolved in preferably an ammoniacal solvent, and in Formula B, the sodium omadine is prepared in water as the solvent. Depending on how a wood is to be used, the wood may be dried after application of the first formula and then treated with the second formula. A well known method called the "empty cell process" can also be used, wherein the first formula is applied in such a manner so as to permit an additional water-borne treatment to occur. The copper salt and sodium omadine react to form the water-insoluble complex inside the treated wood.

Alternatively, the copper:sodium omadine complex, in the ratios shown above, can be formed in water and dissolved in an organic solvent. Alternatively, the two copper salt and organic biocide can be added directly to a suitable organic solvent. The preservative compositions can also be formulated as an emulsion, as described above, and the treatment completed as single step. The oil-borne systems also have the advantage of allowing the wood to be treated in a single step process. Regardless of the application method used, by forming a water-insoluble complex, the present preservative compositions provide non-leacheable biocides for treating wood products that are fixed in the wood and can be effective over a long period of time.

The copper and TBP compositions can also be applied using a dual water-borne treatment when a water soluble form of TBP, a phenolate salt, is used and the copper salt is prepared as an aqueous solution. When the TBP is prepared with an organic solvent, a two-step treatment can also be used. Copper will form a complex with TBP. This complex is dissolved in an organic solvent and the wood is treated in a manner similar to that described above for copper-sodium omadine.

Example 2 below gives the formulation for a two-step treatment using an aqueous copper solution and TBP in an organic solvent based on parts by total weight:

EXAMPLE 2

|  | Broad Range | Preferred Range |
|---|---|---|
| Formula A |  |  |
| Copper | 0.25 to 10.0 | 0.5 to 3.0 |
| Water Solvent | 90 to 99 | 97 to 99 |
| Formula B |  |  |
| TBP | 0.25 to 10.0 | 0.5 to 3.0 |
| Organic Solvent | 90 to 99 | 97 to 99 |
| Ratio of A to B (Copper to TBP) | 20:1 to 1:20 | 8:1 to 1:8 |

Again, the wood can be dried after treatment with the first formula, then followed with treatment with the second formula, or the empty cell process may be used. Alternatively, copper and TBP can be formulated together, such as in an emulsion, and the treatment completed in one step.

The contact between the wood and the mixtures of the present invention can be effected by numerous methods, including brushing, spraying, painting, pressure treating, immersing, etc. Preferably, contact between the wood and the mixtures of the present invention are effective by immersing the wood in the mixture for a period of time which is sufficient to obtain the desired results.

Treating solutions in commercial volumes are typically in the range of:

5,000 to 50,000 gal.

10,000 to 25,000 gal. (preferred)

Contact times with wood may vary from:

0.5 hours to 24 hours 0.5 hours to 3 hours (preferred)

The compositions of the present invention can be used for preserving a wide variety of wood types. Examples of wood species which can be treated with the compositions of the invention include Southern Yellow Pine, Western Red Cedar, Douglas Fir, Inland Fir, Spruce, Hemlock, Sugar Maple, Ash, Walnut, Cherry, White Pine, Red Pine, Birch, Red Oak, White Oak, Elm, Hickory, Linden, Beech, Sycamore, etc.

The compositions of the present invention will also contain at least one solvent/dilutant. The solvent/dilutant may be water or a liquid hydrocarbon. Suitable hydrocarbon liquids include aromatic and aliphatic hydrocarbon solvents such as petroleum hydrocarbon solvents, aromatic hydrocarbons, aromatized petroleum distillates, and mixtures or petroleum hydrocarbon solvents and aromatic hydrocarbon solvents. Examples of useful solvents include xylene, toluene, naphtha, light mineral oil, etc.

The preferred copper salt of the present invention is copper carbonate. However, it is within the scope of the invention to use other copper salts, such as copper sulfate, copper chloride, copper acetate, copper oxide, copper hydroxide, etc. The copper compound is dissolved in preferably an aqueous ammoniacal solution which has a preferred pH range of about 10.8 to 11.0.

The test results below provide determinations of the minimum amount of preservative that is effective in preventing decay of selected species of wood by selected fungi under laboratory conditions and show the synergistic effects of the combinations.

The soil block and agar plate test methods were used to examine the biocidal compositions of the present invention. These commonly used methods are described in *Wood Deterioration And It's Prevention By Preservative Treatments*, Vol.2., edited by D. Nicholas, Syracuse University Press (1973), which is incorporated by reference herein. The soil block method involves impregnating small wood blocks to one or more different retention levels with the biocidal composition. The test blocks were placed on an untreated wood wafer which rested on soil that had been inoculated with a specific wood decay fungus.

Conditioned blocks of wood were impregnated with solutions of preservatives in water or suitable organic solvent to form one or more series of retention levels of the preservative. After a period of conditioning, the impregnated blocks were exposed to a recognized brown-rot wood-destroying fungus. The effectiveness of the biocide is usually determined by measurement of weight loss of the treated wood blocks after a specific incubation period.

When using soil substrates, the soil should have a water-holding capacity between 20 and 40 percent and a pH between 5.0 and 8.0. After breaking up all clumps, the soil was mixed and screened through a U.S. No. 6 sieve and stored in a large covered container. The soil should not be so wet that when sifted the particles again stick together. The oven-dried weight of 118 ml of sifted soil should not be less than 90 grams. The soil is preferably obtained from forested rather than agricultural sites. If the pH of the soil is below 5.0, the soil should be amended with hydrated lime to adjust the pH to between 5.0 and 8.0.

The agar plate method involves the preparation of agar nutrient solutions containing various biocide concentrations. The agar solutions were poured into petri dishes and inoculated with a plug of agar which contained an actively growing fungus culture. The diameter of the fungal culture was measured after a set incubation time. The radial mycelium growth of the fungus on the agar plates which contain biocide was then normalized to the growth on the untreated (control) agar plate. The lowest biocide concentration (parts per million, or ppm) which totally inhibited fungal growth (minimal inhibitory concentration or MIC) was determined. In addition, the concentration of biocide necessary to inhibit the fungal mycelium growth by 50% ($IC_{50}$, ppm, or inhibitory concentration, 50%) was also determined.

The advantages of the agar plate test are that it is rapid (1–2 weeks) and requires a minimal amount of biocide (0.05–0.5 grams). In contrast, the soil block test requires 12–18 weeks and at least one gram of biocide. However, the longer test period of the soil block tests can be used to identify preservative compositions which may be degraded by the fungi.

For the agar plate tests, the biocide concentrations necessary to inhibit the wood decaying fungi are extremely low, and thus the results cannot be related to concentrations actually needed to protect wood in the field, whereas the soil block tests provides an approximation of the biocide concentration required to protect wood in service. The agar plate test gives results which can often be reproduced in subsequent performances of the test, while subsequent soil block tests do not necessarily give reproducible results.

The wood-destroying fungi listed below were used in the following tests.

*P. placenta*=*Postia placenta*, American Type Culture Collection (ATCC) #11538, a brown-rot fungi which is copper tolerant.

*G. trabeum*=*Gloeophyllum trabeum*, ATCC #11539, brown-rotter.

*T. versicolor*=*Trametes versicolor*, ATCC #12679, white-rotter.

*C. globosum*=*Chaetomium globosum*, ATCC #6205, soft-rotter.

*I. lacteus*=*Irpex lacteus*, ATCC #11245, white-rotter.

Table 1 below gives the agar plate results with copper and sodium omadine using four wood destroying fungi. The activity values, $IC_{50}$ and MIC (ppm), for the copper (copper(II) chloride or $CuCl_2$) alone and sodium omadine alone are given, along with the activity values for a combination of three parts copper and one part sodium omadine. The copper solution was tested at 10, 30, 100, 300, and 1000 ppm levels. The copper:sodium omadine (3:1) combination and sodium omadine alone were tested at 3, 10, 30, 100, and 300 ppm levels. As shown in Table 1, the combination of copper:sodium omadine (3:1) results in greater bioactivity values (lower $IC_{50}$ and/or MIC) than either copper or sodium omadine individually.

Synergism is exhibited by the combination having greater activity than each individual component alone when tested at the same concentration. In addition, the synergistic factor (SF) can be calculated. If SF is equal or greater than 1.5, then synergism is indicated (see U. Gisi et al. *Synergistic Interactions of Fungicides with Different Modes of Action*, Trans. Br. Mycol. Soc., 85 (2), at 299–306 (1985)). All SF values calculated using the data in Table 1 are much greater than 1.5.

TABLE 1

AGAR PLATE ACTIVITY VALUES FOR COPPER AND SODIUM OMANDINE.

| Biocide (Solvent) (Biocide Concentration Range) | Copper (Water) (10–1,000 ppm) | Omadine (Water) (3–300 ppm) | Copper:Omadine (Water) (3–300 ppm) |
|---|---|---|---|
| *I. lacteus*; $IC_{50}$/MIC | 53/100 | 7/300 | 2/10 |
| *T. versicolor*; $IC_{50}$/MIC | 95/100 | 8/100 | 3/10 |
| *G. trabeum*; $IC_{50}$/MIC | 67/300 | 32*/100 | 4/30 |
| *P. placenta*, $IC_{50}$/MIC | 167/1000 (300*) | 5/30 | 2/10 |

*Very close to MIC.
$IC_{50}$ Concentration (parts per million) at which the relative fungal growth is inhibited by 50@.
MIC Concentration (parts per million) at which the fungal growth is totally inhibited.
⁼Mutated at 3 ppm.

Additional agar plate tests were carried out using copper solutions (copper(II) chloride), sodium omadine solution, and copper:sodium omadine compositions of ratios of 1:1, 3:1, and 6:1. Water was used as the solvent for all biocides, and the levels tested were 1, 2, 5, 15, 40, and 100 ppms. The four wood destroying fungi used included two brown-rotters, one of which is copper tolerant, one white-rotter and one soft-rotter. The results are shown in Table 2. The 1:1 and 3:1 preservative compositions proved to be synergistic for all four fungi based on reduced MIC values as compared to the individual biocide's MIC values and/or SF values. In addition, for the 6:1 combination, the SF values for three of the four fungi are greater than 1.5 (*P. placenta, T. versicolor,* and *C. globosum*) and are thus considered to be synergistic.

TABLE 2

AGAR PLATE ACTIVITY VALUES OF COPPER AND SODIUM OMADINE.

| Biocides Copper:Sodium Omadine | Solvent | Fungi Activity ($IC_{50}$/MIC, ppm) | | | |
|---|---|---|---|---|---|
| | | *P. placenta* | *G. trabeum* | *T. versicolor* | *C. globosum* |
| 1:0 | Water | >100/>100 | 70/>100 | ~159/>100 | 53/>100 |
| 0:1 | Water | 4/40 | ~2/>100 | 8/>100* | 3/100 |
| 1:1 | Water:Water | 1/15 | 4/40$^{(15*)}$ | 5/100$^{(40*)}$ | 5/40$^{(15*)}$ |
| 3:1 | Water:Water | 5/40 | 5/40 | 6/40 | 8/40 |
| 6:1 | Water:Water | 13/40 | 11/>100 | 8/>100* | 3/>100* |

*Very close to MIC

Additional tests were conducted using the soil block test and the brown-rot fungus *G. trabeum*. Wood blocks were treated using: (1) an aqueous copper salt solution alone (ammoniacal copper solutions); (2) an aqueous sodium omadine solution alone; and (3) different combinations of copper (ammoniacal copper solutions) and sodium omadine. The average retentions, in pounds per cubic foot (pcf), are listed along with the average percent weight loss for the wood blocks in Table 3 below. The results showed the individual biocides at treatment levels of about 0.09 pcf did not offer full protection against the wood destroying fungi-treatments with copper at 0.091 pcf resulting in a 6.0% weight loss and sodium omadine at 0.088 pcf resulting in a 7.8% weight loss.

The combination of copper and sodium omadine, however, at the lower retention level of 0.07 pcf gave essentially complete protection at compositions of 1:1 (0.14% weight loss) and 3:1 (1.21% weight loss). Consequently, synergism is evidenced by the combination of copper and sodium omadine having a greater efficiency at a lower level than either copper or sodium omadine when used alone.

TABLE 3

AVERAGE PERCENT WEIGHT LOSS OF TREATED SOUTHERN PINE BLOCKS EXPOSED TO A BROWN-ROT FUNGUS (*G. TRABEUM*) FOR 8 WEEKS.

| | INDIVIDUAL COMPONENTS | |
|---|---|---|
| Compounds | Avg. Retention (pcf) | Avg. Weight Loss (%) |

TABLE 3-continued

AVERAGE PERCENT WEIGHT LOSS OF TREATED SOUTHERN PINE BLOCKS EXPOSED TO A BROWN-ROT FUNGUS (*G. TRABEUM*) FOR 8 WEEKS.

| Copper | 0.091 | 6.0 |
|---|---|---|
| | 0.187 | 0.7 |
| | 0.392 | 1.0 |
| Omadine | 0.036 | 19.1 |
| | 0.088 | 7.8 |
| | 0.182 | 0.1 |

TABLE 3-continued

AVERAGE PERCENT WEIGHT LOSS OF
TREATED SOUTHERN PINE BLOCKS EXPOSED TO A
BROWN-ROT FUNGUS (G. TRABEUM) FOR 8 WEEKS.

COMBINED COMPONENTS

| Compounds | Avg. Retention Copper/Omadine (pcf) | Total Retention (pcf) | Avg. Weight Loss (%) |
|---|---|---|---|
| Copper & Omadine | 0.035/0.035 | 0.07 | 0.14 |
| | 0.070/0.035 | 0.11 | 0.25 |
| | 0.054/0.018 | 0.07 | 1.21 |
| | 0.102/0.034 | 0.13 | 0.62 |
| Untreated Controls | 0/0 | 0 | 46.2 |

TABLE 4

AVERAGE PERCENT WEIGHT LOSS OF
TREATED SOUTHERN PINE BLOCKS EXPOSED TO A
BROWN-ROT FUNGUS (P. PLACENTA) FOR 8 WEEKS.

INDIVIDUAL COMPONENTS

| Compounds | Avg. Retention (pcf) Weight loss | Avg. Weight Loss (%) |
|---|---|---|
| Copper | 0.188 | 38.6 |
| | 0.385 | 21.6 |
| | 0.778 | 20.1 |
| Omadine | 0.037 | 13.1 |
| | 0.094 | 2.9 |

COMBINED COMPONENTS

| Compounds | Avg. Retention Copper/Omadine (pcf) | Total Retention (pcf) | Avg. Weight Loss (%) |
|---|---|---|---|
| Copper & Omadine | 0.036/0.036 | 0.072 | 4.7 |
| | 0.073/0.037 | 0.110 | 0.9 |
| | 0.110/0.037 | 0.147 | 1.5 |
| Untreated Controls | 0/0 | 0 | 26.0 |

Additional soil block tests were conducted using a copper-tolerant brown-rot fungus, *P. placenta*, and the results are provided in Table 4 above. As can be seen, treatment with only an amnioniacal copper salt solution provided no protection, even at the highest treatment level of 0.778 pcf (20.1% average weight loss). Wood treated with only sodium omadine at 0.037 pcf yielded a 13.1% average weight loss. When copper and sodium omadine were combined, however, increased activity was observed. For example, when a treatment of 0.073 pcf of copper and 0.037 pcf of sodium omadine was used, the average % weight loss was 0.9%, and when a treatment of 0.110 pcf of copper and 0.037 pcf of sodium omadine was used, the average % weight loss was 1.5%.

Table 5 below gives the agar activity values for copper alone, TBP alone and a mixture of copper and TBP (1:1). The levels tested were 5, 10, 25, 60, 150 and 300 ppm. The copper-tolerant brown-rot fungus *P. placenta* and the white-rot fungus *T. versicolor* were used. The SF values are above 1.5 for both fungi.

TABLE 5

AGAR PLATE
ACTIVITY VALUES FOR COPPER AND TBP.

| Biocides | | Fungi Activity $IC_{50}$/MIC, ppm) | |
|---|---|---|---|
| Copper:TBP | Solvent | P. placenta | T. versicolor |
| 1:0 | Water | 165/>300* | 77/>300 |
| 0:1 | Toluene | 7/25 | 16/60 |
| 1:1 | Water:Toluene | 9/25 | 12/60 |

*Indicates a MIC in which the fungus is almost totally inhibited.

The copper and TBP compositions were further tested using the soil block test with a copper tolerant fungus *P. placenta*, and the results are shown in Table 6 below. The wood blocks treated with copper alone resulted in weight loss even at the highest level of treatment, 0.837 pcf. The samples treated with TBP alone resulted in weight loss at 0.157 pcf (6.7% average weight loss). The preservative compositions of copper and TBP (0.085 pcf of copper and 0.085 pcf of TBP) resulted in only 5.2% average weight loss, and the samples treated with 0.154 pcf of copper and 0.077 pcf of TBP resulted in only 1.4% average weight loss.

TABLE 6

AVERAGE PERCENT
WEIGHT LOSS OF TREATED SOUTHERN
PINE BLOCKS EXPOSED TO A COPPER TOLERANT
BROWN-ROT FUNGUS (P. PLACENTA) FOR 8 WEEKS.

INDIVIDUAL COMPONENTS

| Compounds | Avg. Retention (pcf) | Avg. Weight Loss (%) |
|---|---|---|
| Copper | 0.099 | 45.4 |
| | 0.202 | 51.8 |
| | 0.412 | 42.1 |
| | 0.837 | 29.3 |
| TBP | 0.081 | 33.6 |
| | 0.157 | 6.7 |
| | 0.337 | 0.6 |
| | 0.642 | 0.4 |

COMBINED COMPONENTS

| Compounds | Avg. Ret., pcf Copper:TBP | Total Retention, pcf | Avg. Wt. Loss (%) |
|---|---|---|---|
| Copper:TBP | 0.085:0.085 | 0.170 | 5.2 |
| | 0.165:0.165 | 0.330 | 0.1 |
| | 0.154:0.077 | 0.231 | 1.4 |
| | 0.099:0.197 | 0.296 | 0.8 |
| Control | — | — | 38.2 |

The foregoing soil block tests were conducted using a conditioning room maintained at temperatures of approximately 20° and 30° C. and an average relative humidity between 25 and 75%. The selected temperature was not varied by more than ±2° C. (±4° F.). The incubation room was maintained at a selected temperature between 25° and 27° C. (77° and 81°) and an average relative humidity between 65 and 75%. The selected temperature was varied by more than ±2° C. (±4°) and the selected humidity not more than ±5%. Lights remained off during decay tests except when needed for period inspection.

The wood used in the test came from newly cut boards, nominally 1 inch thick, that are immediately kiln-dried without anti-stain treatment to provide chemically free wood that has had minimum opportunity for fungus infection or deterioration before use in the soil-block.

The treating solutions of the preservative must be carefully prepared in appropriate concentrations. The concentration of the preservatives to be used should provide a uniform distribution of preservative at retentions low enough to permit fungus attack and to determine the threshold values for the various test fungi employed.

Finally, since numerous modifications and changes will readily occur to those skilled in the art, it is not desired to limit the invention to the exact construction and operation shown and described, and accordingly all suitable modification and equivalents may fall within the scope of the invention.

The present invention has been described in terms of a preferred embodiment and is considered as illustrative only of the principles of the invention. The invention, however, is not limited to the embodiment depicted and described.

What is claimed is:

1. A biocidal composition for preserving wood having improved efficacy comprising a combination of:
   (a) a copper salt; and
   (b) an organic biocide selected from the group consisting of tribromophenol, the salts and chelates of tribromophenol, and sodium pyrithione, and the chelates thereof, wherein the combination forms a complex that is substantially non-leachable from wood and wherein the weight ratio of copper to tribromophenol is in the range of about 20:1 to 1:20, and the weight ratio of copper to sodium pyrithione is about 20:1 to 1:2.

2. A composition according to claim 1 wherein the copper salt is dissolved in an aqueous ammoniacal solution having a pH range of about 10.8 to 11.0.

3. A composition according to claim 1 wherein the combination of copper salt and organic biocide is prepared as an emulsion.

4. A composition according to claim 1 wherein the weight ratio of copper to tribromophenol is in the range of about 8:1 to 1:8.

5. A composition according to claim 1 wherein the weight ratio of copper to sodium pyrithione is in the range of about 10:1 to 2:1.

6. A composition according to claim 1 wherein said copper salt is copper carbonate.

7. A composition according to claim 1 further containing additives comprising one or more of anti-foam agents, surfactants, anti-oxidants, flame retardants, coloring agents, insecticides, deodorants, malicides and stabilizing agents in amount in the range of about 0.1 to 10.0 percent by weight.

* * * * *